United States Patent [19]

Watanabe

[11] Patent Number: 5,009,591
[45] Date of Patent: Apr. 23, 1991

[54] PYROLYZER FOR GAS CHROMATOGRAPHY

[75] Inventor: Chuichi Watanabe, Gotemba, Japan

[73] Assignee: The Dow Chemical Company, Midland, Mich.

[21] Appl. No.: 472,532

[22] Filed: Jan. 30, 1990

[30] Foreign Application Priority Data

Jan. 30, 1989 [JP] Japan .................................. 1-17443

[51] Int. Cl.$^5$ .............................................. F27B 9/02
[52] U.S. Cl. ................................... 432/128; 432/152; 432/253; 432/227
[58] Field of Search ............... 432/227, 229, 230, 231, 432/152, 253, 128

[56] References Cited

U.S. PATENT DOCUMENTS

| | | | |
|---|---|---|---|
| 4,412,812 | 11/1983 | Sadowski et al. | 432/253 |
| 4,586,898 | 5/1986 | Orbeck | 432/128 |
| 4,610,628 | 9/1986 | Mizushina | 432/253 |
| 4,627,814 | 12/1986 | Hattori et al. | 432/128 |
| 4,752,216 | 6/1988 | Hurrell | 432/152 |

OTHER PUBLICATIONS

J. Chih-An Hu, *Chromatopyrography Analysis of Rubbers and Other High Polymers*, Journal of Chromatographic Science, 19, (Dec. 1981).

S. Liebman, E. Levy, *Advances in Pyrolysis GC Systems: Applications to Modern Trace Organic Anlaysis*, Journal of Chromatographic Science, 21, (Jan. 1983).

N. Iglauer, F. Bentley, *Pyrolysis GLC for the Rapid Identification of Organic Polymers*, Journal of Chromatographic Science, 12, 23-33 (Jan. 1974).

*Primary Examiner*—Henry C. Yuen
*Attorney, Agent, or Firm*—Timothy S. Stevens

[57] ABSTRACT

A pyrolyzer for gas chromatography having a subsidiary heater and a main heater. The subsidiary heater is set below the pyrolysis temperature of the sample, e.g., at 300 degrees centigrade, to drive volatile components from the sample. The main heater is set at a pyrolysis temperature to pyrolize the sample, e.g., at 600 degrees centigrade. The sample is placed in the pyrolyzer in a sample vessel that can be positioned to be heated by main heater, the subsidiary heater and a position not heated by either the main heater or the subsidiary heater.

3 Claims, 3 Drawing Sheets

PYROLYZER FOR GAS CHROMATOGRAPHY

FIELD OF THE INVENTION

The present invention is in the field of gas chromatography and more particularly in the field of pyrolysis gas chromatography apparatus.

BACKGROUND OF THE INVENTION

Pyrolysis gas chromatography is an important chemical analysis method. According to this method, a specific substance to be analyzed is decomposed by heating to generate a number of decomposition products which are then determined by gas chromatography.

In this pyrolyzing chromatography, in the case where the specific substance to be analyzed is accompanied by other volatile substance, if this mixture sample is heated at a temperature lower than the pyrolyzing temperature of the specific substance to volatilize the volatile substance, the volatile substance is analyzed by the gas chromatography if necessary and the sample is then heated at the pyrolyzing temperature and the intended pyrolyzation is carried out, the pyrolyzing chromatography of the specific substance can be precisely performed and the accompanying other substance can be simultaneously analyzed. Therefore, the method will be very convenient and advantageous.

However, an appropriate apparatus for carrying out this method has not been known.

There is known an apparatus comprising only a heater for pyrolyzing sample components. However, when this apparatus is used, it is impossible to separate a volatile component by volatilization before the pyrolyzation of the intended substance. Furthermore, there is known an apparatus of the type where a heater for the pyrolyzation is placed in a heating block preheated at 200° C. to 300° C. When this apparatus is used, a sample is inserted into the heating block in the state where the heater for the pyrolyzation is not actuated, a volatile component is volatilized at a temperature lower than the pyrolyzing temperature by heating by the heating block and the volatile substance is analyzed, and then, the heater for the pyrolyzation is actuated to perform the pyrolyzation of the sample and the pyrolyzation products are analyzed. However, this method is still insufficient in the following point. During a relatively long period of from the point of completion of the volatilization of the volatile component to the point of termination of the analysis of the volatile component by the gas chromatography, for example, during a period of 20 to 40 minutes, the sample is kept exposed to the temperature of the heating block, and especially if air is incorporated into a carrier gas passage at the time of charging of the sample, an undesirable reaction of the sample, such as oxidation, is advanced and precise analysis becomes difficult.

SUMMARY OF THE INVENTION

Therefore, the present invention is to provide a pyrolyzer which has not only a pyrolyzing function but also a function of performing preheating for a time necessary for volatilizing a volatile component in a sample prior to the pyrolyzation.

In accordance with the present invention, this problem is solved by a pyrolyzer for the pyrolyzing gas chromatography, having a main heater for pyrolysis of a sample to be analyzed and a subheater for heating the sample at a temperature lower than a temperature of the main heater, wherein a sample container can be moved among a position heated by the main heater, a position heated by the subheater and a position not heated by both the main heater and subheater, in the pyrolyzer.

BRIEF SUMMARY OF THE DRAWINGS

FIG. 3 C is a gas chromatogram obtained using a prior art gas chromatography pyrolyzer.

DETAILED DESCRIPTION OF THE INVENTION

Figure 1:
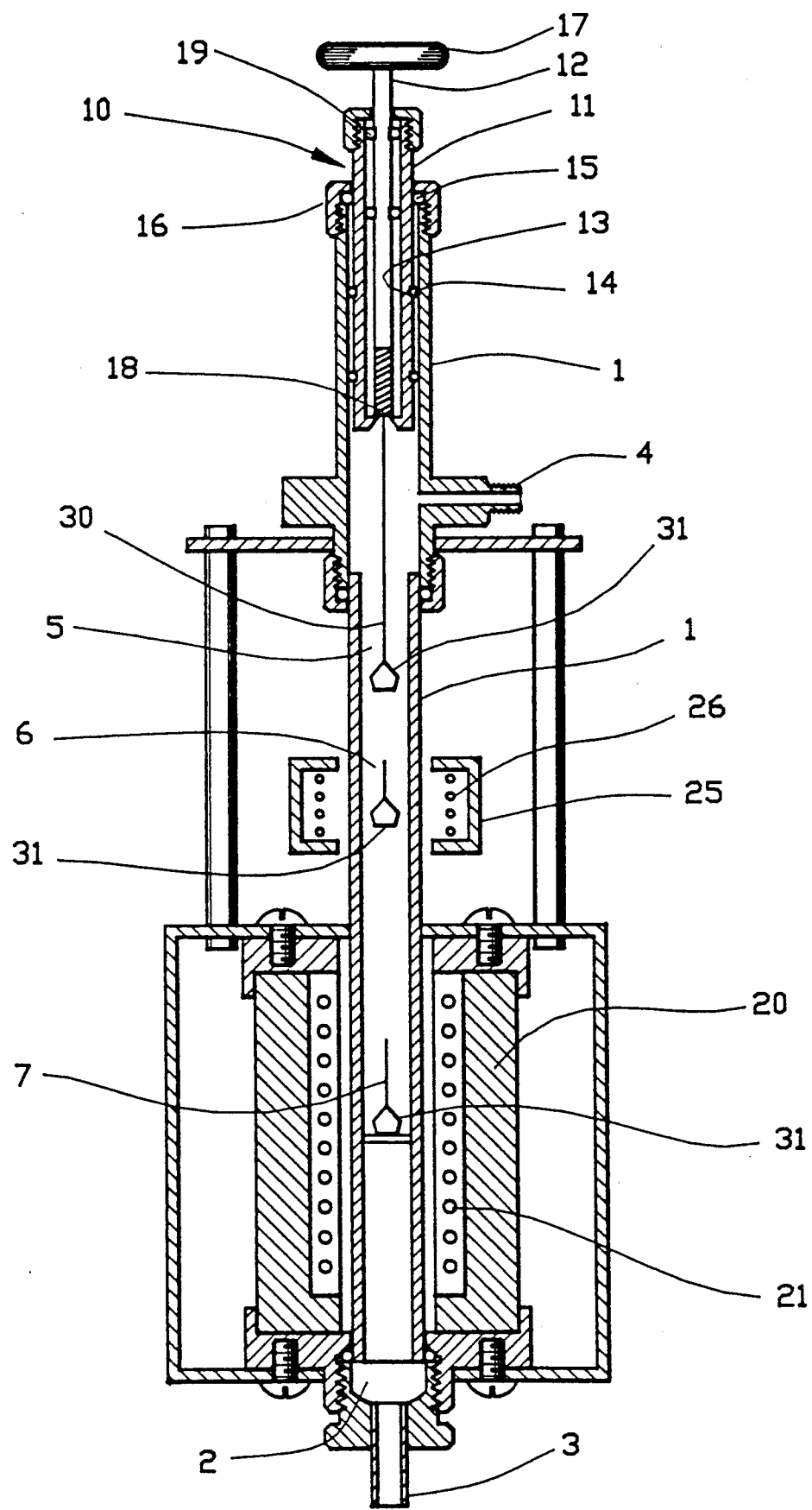
FIG. 1 is a cross-sectional drawing of a pyrolysis gas chromatography apparatus according to the present invention showing a sample vessel which is vertically positionable between an unheated zone, a subheated zone and a main heated zone.

One embodiment of the apparatus of the present invention is illustrated in FIG. 1. This apparatus comprises a pyrolyzing cylinder 1, a sample delivery rod 10, a main heater 20, a subsidiary heater 25 and a sample holding rod 30.

The pyrolyzing cylinder 1 is preferably formed of an upper part of a metal and a lower part of quartz, and a bottom 2 is closed and a carrier gas outlet 3 is formed in this bottom. The other end is opened and a carrier gas inlet 4 is formed at an intermediate part.

When the apparatus is used, the sample delivery rod 10 is inserted from the open end of the pyrolyzing cylinder 1. This sample delivery rod 10 has an outer cylinder 11 and an operating rod 12 and is movable relatively to the pyrolyzing cylinder 1. The outer surface of the outer cylinder 11 is air-tightly contacted with the inner surface of the pyrolyzing cylinder 1. This air-tight contact can be accomplished by an any conventional method. For example, front-face slip contact can be attained between the outer surface of the outer cylinder 11 of the sample delivery rod 10 and the inner surface of the pyrolyzing cylinder 1. However, in order to facilitate the movement of the sample delivery rod 10 while keeping air tightness, it is preferred that a slight clearance be formed between the outer surface of the outer cylinder 11 of the sample delivery rod 10 and the inner surface of the thermal decomposition cylinder 1, a circular groove 13 be formed on the surface of the outer cylinder 11 of the sample delivery rod 10 and an O-ring 14 be arranged in this groove. The number of the O-ring is not particularly critical, but about two of O-rings are preferably formed. In order to maintain air tightness, it is preferred that a claviform inclination be formed on the inner surface of the open end of the thermal decomposition cylinder 1, an O-ring 15 be arranged between this inner inclined surface and the outer surface of the outer cylinder 11 and the O-ring be pressed by a pressing member, for example, a nut 16.

The outer cylinder 11 has an operating rod 12 inserted therein. The operating rod 12 pieces through the outer cylinder 11 and a knob 17 is attached to the outer end of the operating rod 12, and by operating this knob, an attaching and detaching mechanism 18 disposed on the other end of the operating rod 12 for effecting attachment and detachment between the sample holding rod 30 and the top end of the outer cylinder 11 of the sample delivery rod 10 can be operated. The operating rod 12 is movable relatively to the outer cylinder 11 and is air-tightly contacted with the inner surface of the outer cylinder 11. This air-tight contact can be accomplished by an any conventional method. For example, front-face slip contact can be attained between the inner surface of the outer cylinder 11 and the outer surface of the operating rod 12. However, in order to maintain air tightness assuredly, it is preferred that a clearance be formed between the outer surface of the operating rod 12 and the inner surface of the outer cylinder 11 and an O-ring 19 be arranged in this clearance.

Conventional means can be adopted as the attaching and detaching mechanism 18 for effecting attachment and detachment between the sample holding rod 30 and the top end of the outer cylinder 11, so far as the attaching and detaching operations can be performed from the outside through the operating rod 12 by the operation of the knob 17.

Various conventional heaters can be used as the main heater 30 and subsidiary heater 25, so far as a sample in the pyrolyzing cylinder can be heated at a predetermined temperature within a short time. Preferably, electric heaters 21 and 26 are arranged outside the pyrolyzing cylinder, and the sample in the cylinder is heated by heating predetermined parts of the cylindrical portion of the pyrolyzing heater. The main heater 20 is ordinarily disposed in the vicinity of the bottom 2 of the pyrolyzing cylinder and the subsidiary heater 25 is disposed on the open end side of the pyrolyzing cylinder with a certain distance from the main heater. This distance is one sufficient to avoid the influence of the main heating so that the predetermined temperature lower than the temperature by the main heating is maintained at the heating position by the subsidiary heater 25. In the region of this distance, the temperature is maintained at a level higher than the temperature set by the subsidiary heater 25 by heat transfer or the like, so that the volatilized component is not condensed. The heating temperature by the main heater in the pyrolyzing cylinder 10 is 300° C. to 1000° C., and the temperature can be adjusted to a predetermined level by a temperature-adjusting device (not shown in the drawings). The heating temperature by the subsidiary heater 25 in the pyrolyzing cylinder is 50° C. to 400° C., and this temperature is adjusted to a predetermined level by a temperature-adjusting device (not shown in the drawings).

The sample holding rod 30 has a sample vessel 31 on one end, and the other end is attached to the attaching and detaching mechanism 18 arranged on the top end of the sample delivery rod 10. The length of the sample holding rod 30 is such that in the case where the sample delivery rod 10 is inserted into the pyrolyzing cylinder 1 to locate the sample vessel 31 at the subsidiary heating position 6, the carrier gas inlet 4 is not shut by the sample delivery rod 10. The sample vessel 31 and sample holding rod 30 are formed of a heat-resistant and corrosion-resistant material such as a metal, preferably nickel or platinum.

The apparatus shown in FIG. 1 is manipulated in the following manner. At first, the subsidiary heater 25 and main heater 20 are actuated, and the predetermined parts of the pyrolyzing cylinder are heated at predetermined temperatures. For example, the main heating position is heated at the pyrolyzing temperature of 600° C. and the subsidiary heating position is heated at the volatilization temperature of 300° C. On the other hand, a predetermined amount of a sample is charged in the sample vessel 31, and one end of the sample holding rod 31 is attached to the attaching and detaching mechanism 18. The sample delivery rod 10 is inserted into the pyrolyzing cylinder to a position 5 where the sample vessel 31 does not reach the subsidiary heating position 6. Then, in this state, a carrier gas is introduced for a certain time and air in the pyrolyzing cylinder is completely replaced by the carrier gas. When the flow rate of the carrier gas is 100 ml/min (in the case where the inner diameter of the thermal decomposition cylinder is 6 mm), this time is calculated to be 0.6 second, but practically, a time of up to about 20 seconds is sufficient. Then, the sample delivery rod 10 is further inserted so that the sample vessel 31 arrives at the subsidiary heating position 6. Thus, the sample in the sample vessel 31 is heated at the volatilization temperature, for example, 300° C., and the volatile component in the sample is evaporated. Since the evaporation is ordinarily completed within 2 to 5 minutes though the time differs to some extent according to the vapor pressure of the vaporized substance, after the lapse of this time the sample delivery rod 10 is drawn up and the sample vessel 31 is returned to the non-heating position. The volatilized substance is introduced into a separating column (not shown in the drawings) and analyzed by the gas chromatography. After completion of this analysis, the knob 17 of tho operating rod 12 is operated to separate the sample holding rod 30 from the sample delivery rod 10, and the holding rod 30 together with the sample vessel 31 is let to fall down to the main heating position 7 where the component in the sample is decomposed at the pyrolyzing temperature, and the decomposition products are subsequently analyzed by the chromatography.

Figure 2:
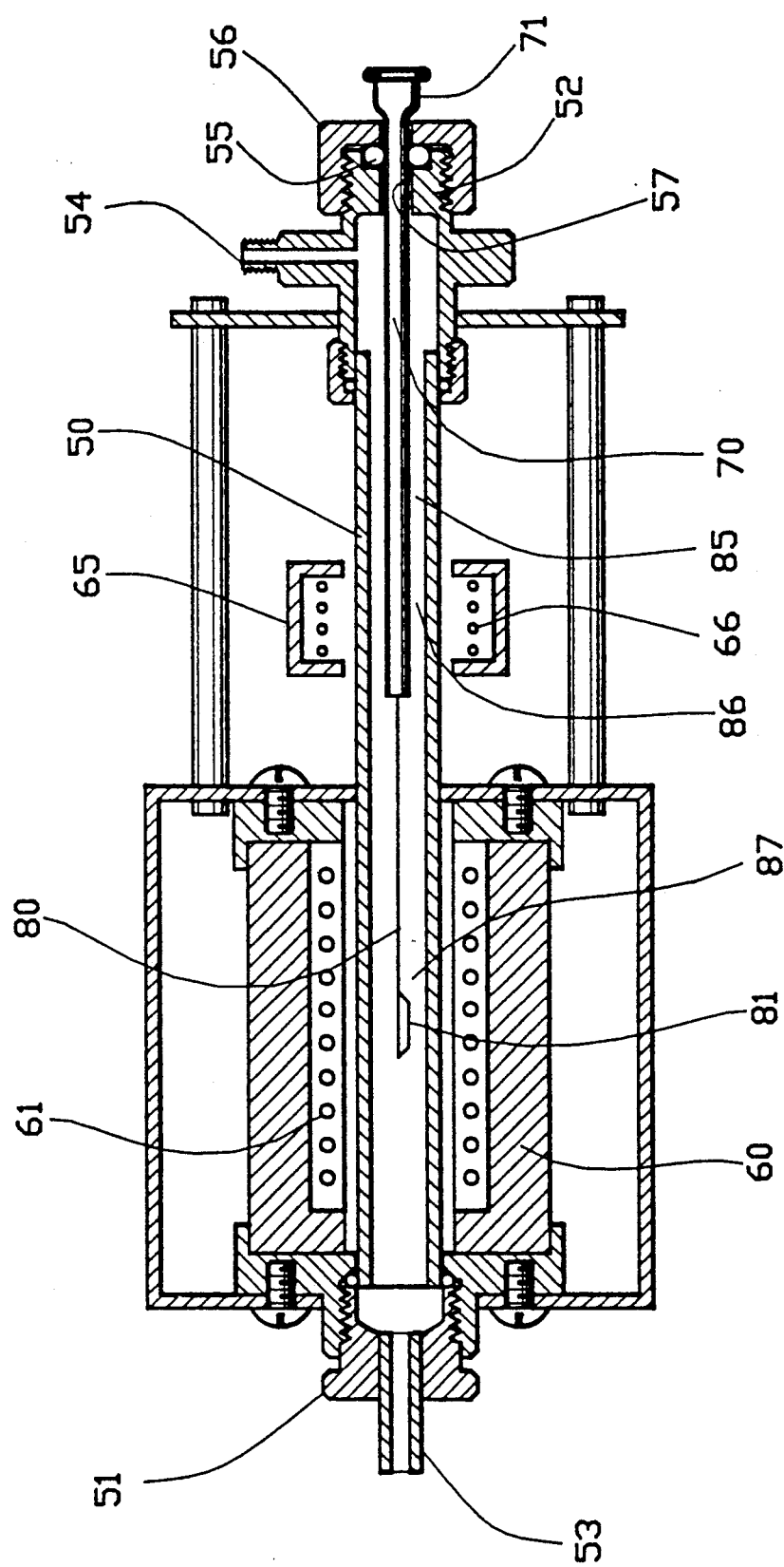
FIG. 2 is a cross-sectional drawing of another pyrolysis gas chromatography apparatus according to the present invention showing a sample vessel which is horizontally positionable between an unheated zone, a subheated zone and a main heated zone.

FIG. 2 illustrates another embodiment of the apparatus of the present invention. This apparatus comprises a pyrolyzing tube 50, a main heater 60, a subsidiary heater 65, a sample delivery rod 70 and a sample holding rod 80. The pyrolyzing tube 50 has a rear end cap 51 having a carrier gas outlet 53 at the rear end and a front end cap 52 having a carrier gas inlet 54. The main heater 60 and subsidiary heater 65 are, for example, electric heaters having electric heating wires 61 and 66, and the temperature control is performed in the same manner as in the apparatus shown in FIG. 1. One end of the sample holding rod 80 is attached to the top end of the sample delivery rod 70, and a sample vessel 81 is arranged on the other end of the sample holding rod 80. The sample delivery rod 70 is movably and air-tightly inserted into the pyrolyzing tube 50 through a piercing hole 57 at the end portion of the front end cap 52. This air tightness is maintained by an O-ring 55 arranged on the top end of the front end cap 52 and a pressing nut 56. If this structure is adopted, by pushing and pulling the knob 71 of the sample delivery rod 70, the sample vessel 18 can be optionally moved among the non-heating position 85, subsidiary heating position 86 and main heating position 87.

When this apparatus is used, both the heaters are actuated and the predetermined positions of the pyrolyzing tube 50 are heated at predetermined temperatures. On the other hand, the sample delivery rod 70 and sample holding rod 80 are pulled out and a predetermined sample is charged into the sample vessel 81. Then, the rod is inserted into the pyrolyzing tube 50 so that the sample vessel 81 is located at the non-heating position. A carrier gas is caused to flow and air in the pyrolyzing tube is completely replaced by the carrier gas, and then, the knob 71 is pushed in and the sample vessel 81 is shifted to the subsidiary heating position 86 where the volatile component in the sample is volatilized at the subsidiary heating temperature, for example, 300° C. After termination of the vaporization, for example, after the passage of 2 to 5 minutes, the knob 71 is pulled out again and the sample vessel 81 is returned to the non-heating position 85. In this state, the volatile component is analyzed by the chromatography, for example, for 10 to 20 minutes. After completion of the pyrolyzation of the volatile component, the sample vessel is shifted to the main heating position 87 and the sample component is pyrolyzed at the pyrolyzing temperature, for example, 600° C. The decomposition products are subsequently analyzed by the gas chromatography.

According to the apparatus of the present invention, the sample vessel can be moved among the non-heating position, the subsidiary heating position (maintained at the temperature volatilizing the volatile component) and the main heating position (maintained at the temperature pyrolyzing the sample component). Therefore, it is possible to perform such operations that the carrier gas is introduced to replace air by the carrier gas while locating the sample vessel at the non-heating position, the sample vessel is then moved to the subsidiary heating position and held at this position only for a time necessary for volatilization of the volatile component and the sample is returned to the non-heating position and held at this position during the period of from the point of termination of the volatilization to the point of completion of the analysis of the volatile component.

COMPARATIVE EXAMPLE

Figure 3A:
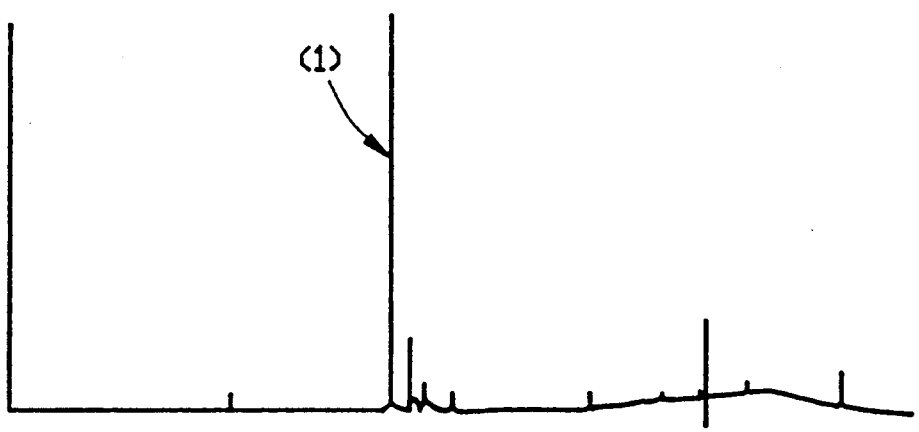
FIG. 3 A and 3 B are gas chromatograms obtained using the present invention.
Figure 3B:
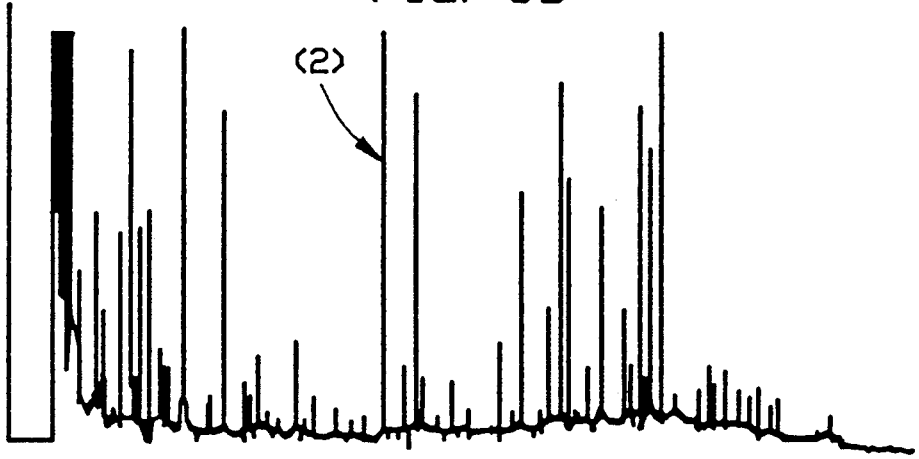
Figure 3C:
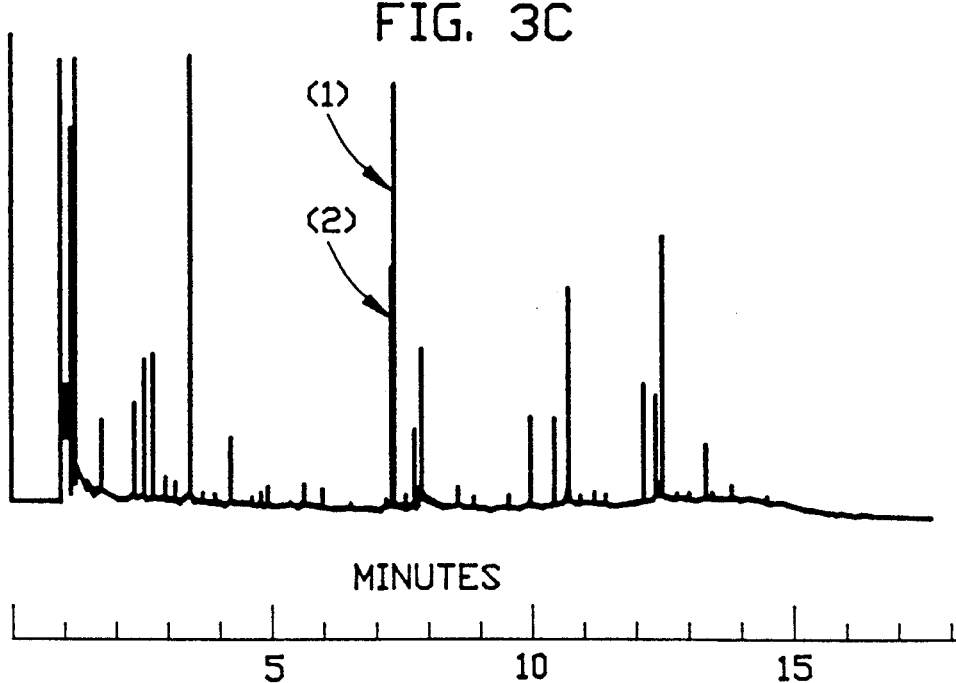

A polyurethane foam is analyzed using prior art pyrolysis gas chromatography apparatus set for a pyrolysis temperature of 600 degrees centigrade. The foam is composed of a polymer comprising a polyol, styrene, acrylonitrile and toluene diisocyanate as well as a small amount of monomeric toluene diisocyanate. The resulting chromatogram is shown in FIG. 3 C. In FIG. 3 C, peak (1) is toluene diisocyanate which is a volatile component of the foam and peak (2) is styrene dimer which is a pyrolysis product of the foam. In FIG. 3 C, peak (1) and peak (2) substantially overlap each other.

EXAMPLE

The prior art pyrolyzer of the Comparative Example is replaced with the pyrolizer shown in FIG. 1. The subsidiary heater is set at 300 degrees centigrade and the main heater is set at 600 degrees centigrade. The same sample of polyurethane foam is analyzed according to the present invention at these two temperatures, i.e., at 300 degrees centigrade for ten minutes and then at 600 degrees centigrade to produce the chromatograms shown in FIG. 3 A and FIG. 3 B respectively. In FIG. 3 A, peak (1) is toluene diisocyanate which is a volatile component of the foam. In FIG. 3 B, peak (2) is styrene dimer which is a pyrolysis product of the foam. This example shows a benefit of the present invention, i.e., the complete separation of peak (1) and peak (2).

What is claimed is:

1. A gas chromatography pyrolyzer apparatus comprising:
   (a) a body defining a cavity therein, the cavity having at least a first portion, a second portion and a third portion, the body also defining a carrier gas inlet port therethrough in fluid communication with the cavity, the body further defining a carrier gas outlet port therethrough in fluid communication with the cavity so that a carrier gas can be flowed into the cavity through the carrier gas inlet port and then out of the cavity through the carrier gas outlet port to sweep any pyrolysis products generated in the cavity out of the carrier gas outlet port so that any pyrolysis products generated in the cavity can be analyzed by gas chromatography;
   (b) a movable sample vessel positioned within the cavity for containing a sample to be pyrolyzed;
   (c) a subsidiary heater for heating the second portion of the cavity;
   (d) a subsidiary heater for heating the third portion of the cavity;
   (e) means for selectively positioning the sample vessel at the first, second or third portions of the cavity so that a sample contained in the sample vessel is essentially not heated when the sample vessel is positioned at the first portion of the cavity, can be heated to a temperature below its pyrolysis temperature when the sample vessel is position at the second portion of the cavity and can be heated to its pyrolysis temperature when the sample vessel is position at the third portion of the cavity.

2. The apparatus of claim 1 wherein the subsidiary heater heats the second portion of the cavity to a temperature of between 50 and 400 degrees centigrade and the main heater heats the third portion of the cavity to a temperature of between 300 and 1000 degrees centigrade.

3. The apparatus of claim 1 wherein the body comprises a quartz cylinder, the quartz cylinder having a bore therethrough, the bore comprising the cavity.

* * * * *